US009804075B2

(12) United States Patent
Otsuka et al.

(10) Patent No.: US 9,804,075 B2
(45) Date of Patent: Oct. 31, 2017

(54) PARTICLE SORTING APPARATUS, PARTICLE SORTING METHOD, AND NON-TRANSITORY COMPUTER-READABLE STORAGE MEDIUM STORING PROGRAM

(71) Applicant: SONY CORPORATION, Tokyo (JP)

(72) Inventors: Fumitaka Otsuka, Tokyo (JP); Hiroto Kasai, Tokyo (JP); Takashi Miyata, Tokyo (JP); Takayuki Kato, Chiba (JP); Kouhei Hatamoto, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/115,812

(22) PCT Filed: Feb. 5, 2015

(86) PCT No.: PCT/JP2015/000524
§ 371 (c)(1),
(2) Date: Aug. 1, 2016

(87) PCT Pub. No.: WO2015/122160
PCT Pub. Date: Aug. 20, 2015

(65) Prior Publication Data
US 2017/0010203 A1   Jan. 12, 2017

(30) Foreign Application Priority Data

Feb. 14, 2014 (JP) .................................. 2014-026620

(51) Int. Cl.
*B03B 1/00* (2006.01)
*G01N 15/14* (2006.01)
(Continued)

(52) U.S. Cl.
CPC ........ *G01N 15/1404* (2013.01); *B01L 3/0268* (2013.01); *B01L 3/502715* (2013.01);
(Continued)

(58) Field of Classification Search
CPC .......... B07C 5/3425; G01N 2015/0019; G01N 15/1404
(Continued)

(56) References Cited

U.S. PATENT DOCUMENTS 6,372,506 B1 *  4/2002  Norton ............... G01N 15/1404
                                                      209/127.4
6,809,804 B1 * 10/2004  Yount ................ G01N 15/1459
                                                       250/214 DC
(Continued)

FOREIGN PATENT DOCUMENTS

JP   2007-532874 A    11/2007
JP   2010-510782 A     4/2010
(Continued)

*Primary Examiner* — Terrell Matthews
(74) *Attorney, Agent, or Firm* — Chip Law Group

(57) ABSTRACT

The present disclosure provides a particle sorting apparatus, a particle sorting method, and a non-transitory computer-readable storage medium storing program that enable sorting object particles to be sorted with high precision, even when the sorting object particles are large. In the particle sorting apparatus, a charging unit that applies charges to at least a part of liquid droplets ejected from an orifice to generate a fluid stream and a charging control unit that adjusts a charge application end time in the charging unit according to sizes of particles included in the liquid droplets are provided.

12 Claims, 16 Drawing Sheets

(51) Int. Cl.
*B01L 3/02* (2006.01)
*B01L 3/00* (2006.01)
*B07C 5/342* (2006.01)
*G01N 15/10* (2006.01)
*G01N 15/00* (2006.01)

(52) U.S. Cl.
CPC ...... *B01L 3/502776* (2013.01); *B07C 5/3425* (2013.01); *G01N 15/1459* (2013.01); *B01L 2200/0652* (2013.01); *B01L 2300/0645* (2013.01); *B01L 2300/0816* (2013.01); *B01L 2300/0864* (2013.01); *B01L 2400/049* (2013.01); *B01L 2400/0415* (2013.01); *B01L 2400/0439* (2013.01); *G01N 2015/0019* (2013.01); *G01N 2015/1006* (2013.01); *G01N 2015/1406* (2013.01); *G01N 2015/149* (2013.01)

(58) Field of Classification Search
USPC .......................................................... 209/4
See application file for complete search history.

(56) References Cited

U.S. PATENT DOCUMENTS

| | | | | |
|---|---|---|---|---|
| 8,975,595 | B2* | 3/2015 | Norton | G01N 15/14 250/428 |
| 8,994,329 | B2* | 3/2015 | Ohkuma | H01M 10/44 180/65.1 |
| 9,162,229 | B2* | 10/2015 | Gaskill-Fox | B01L 9/52 |
| 9,222,872 | B2* | 12/2015 | Buchanan | G01N 15/1404 |
| 2008/0293146 | A1* | 11/2008 | Frazier | G01N 15/1404 436/63 |
| 2011/0284378 | A1 | 11/2011 | Shinoda | |
| 2012/0276544 | A1 | 11/2012 | Quake et al. | |
| 2013/0258075 | A1* | 10/2013 | Muraki | G01N 15/14 348/61 |
| 2015/0285726 | A1* | 10/2015 | Tanase | G01N 15/1459 209/4 |

FOREIGN PATENT DOCUMENTS

| | | |
|---|---|---|
| JP | 2010-190680 A | 9/2010 |
| WO | 2015/056516 A | 4/2015 |

* cited by examiner

[Fig. 1]
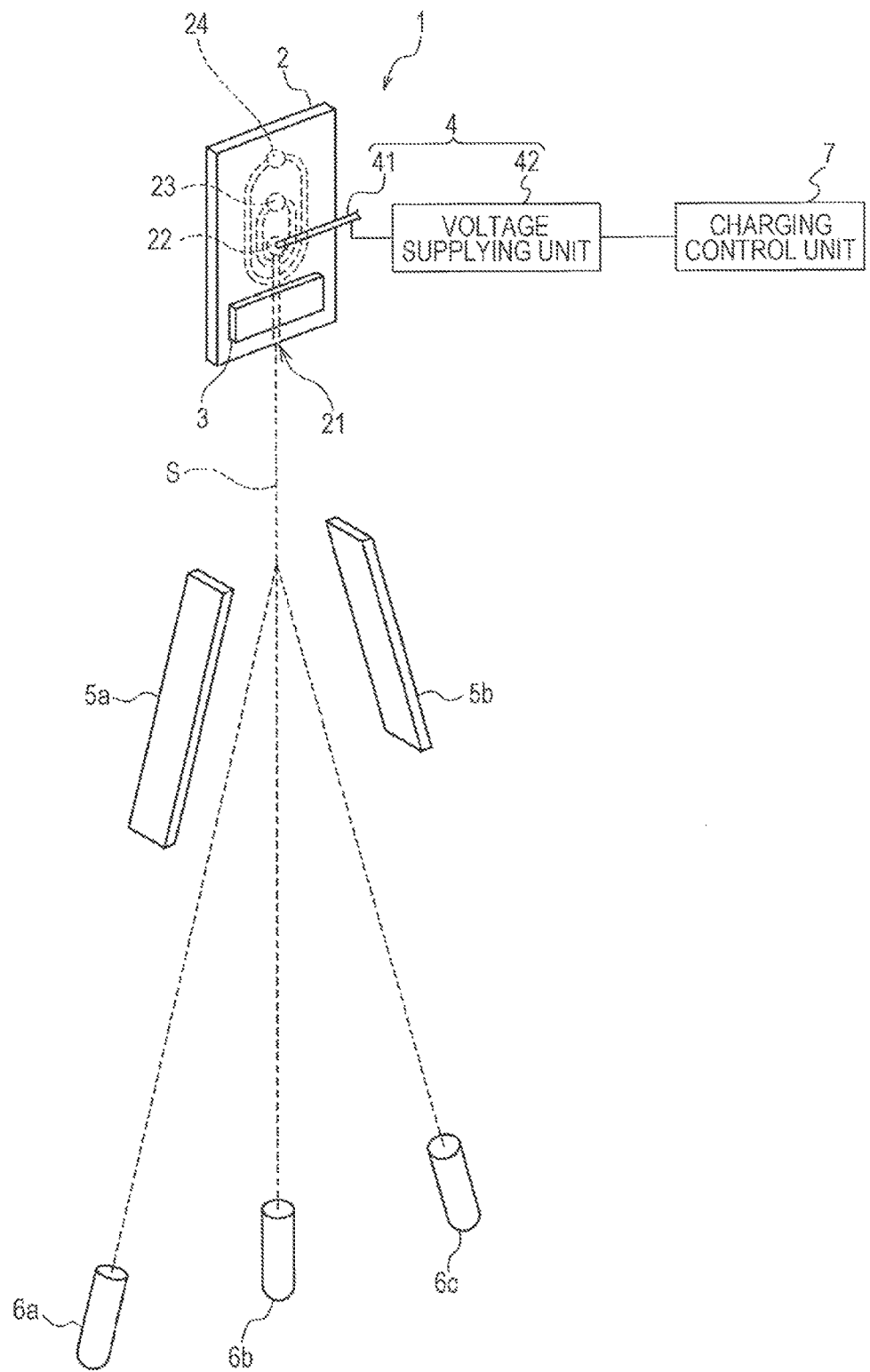

[Fig. 2]
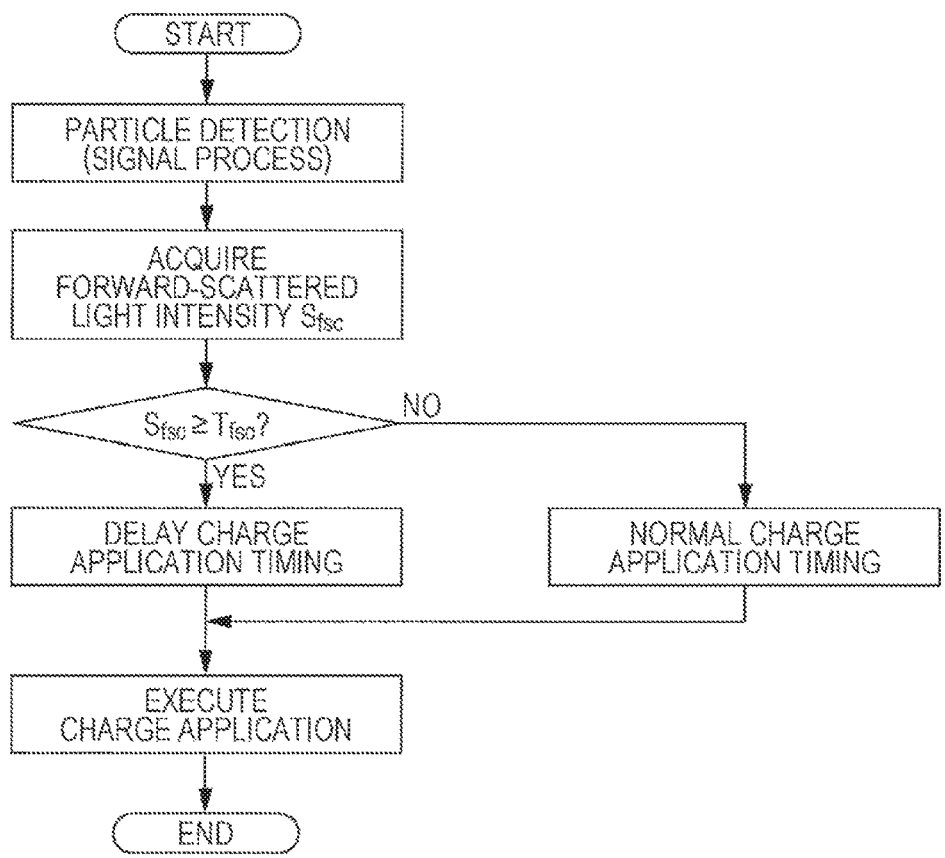

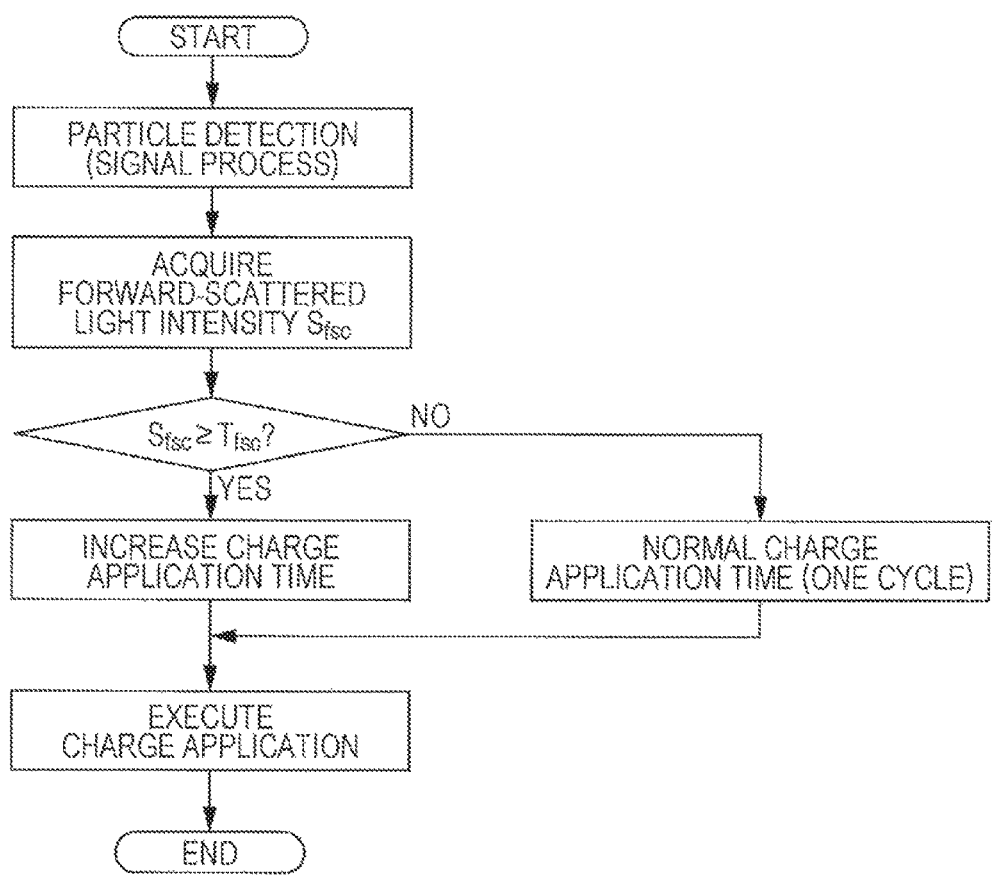
[Fig. 3]

[Fig. 4]
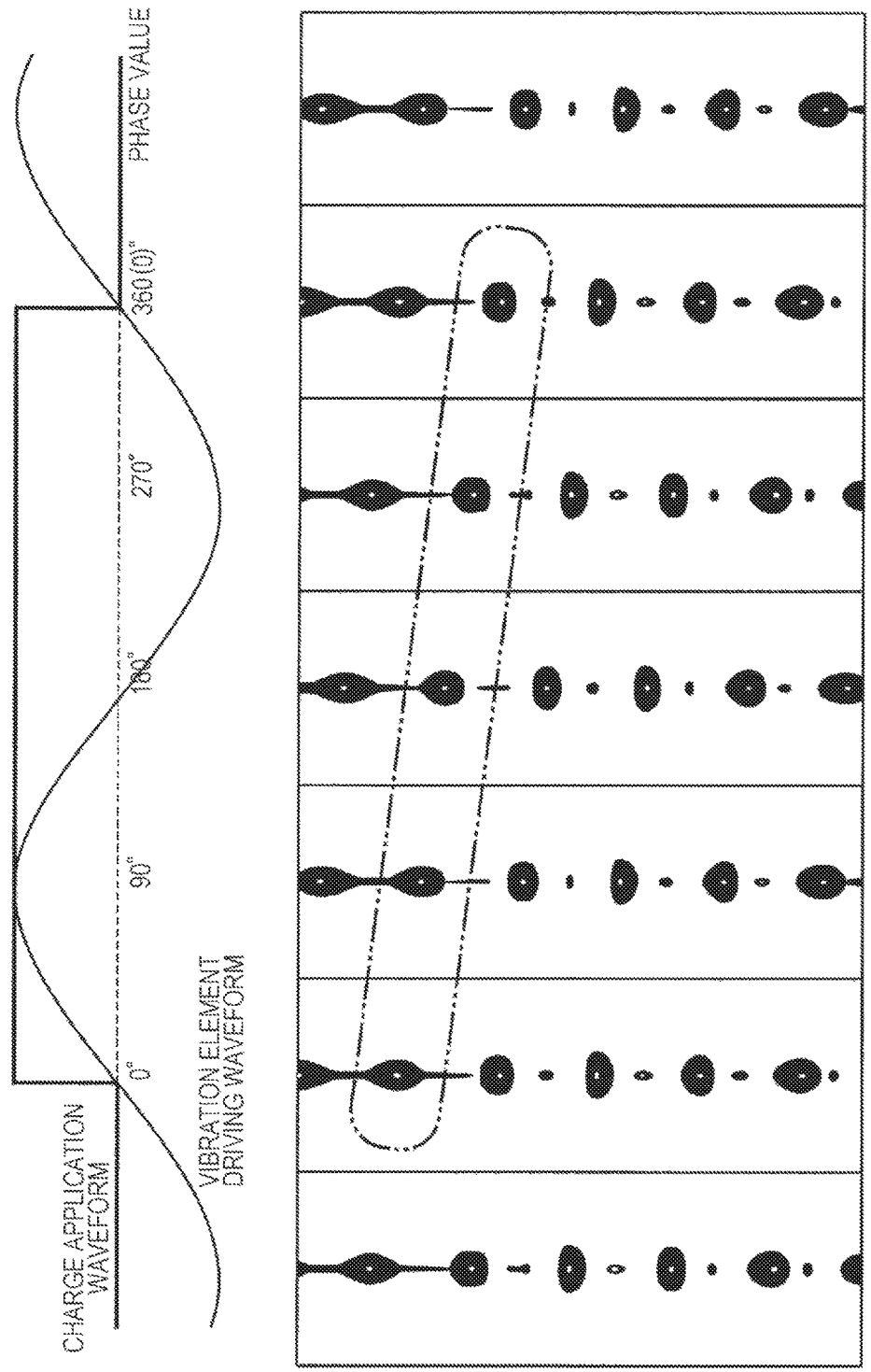

[Fig. 5]
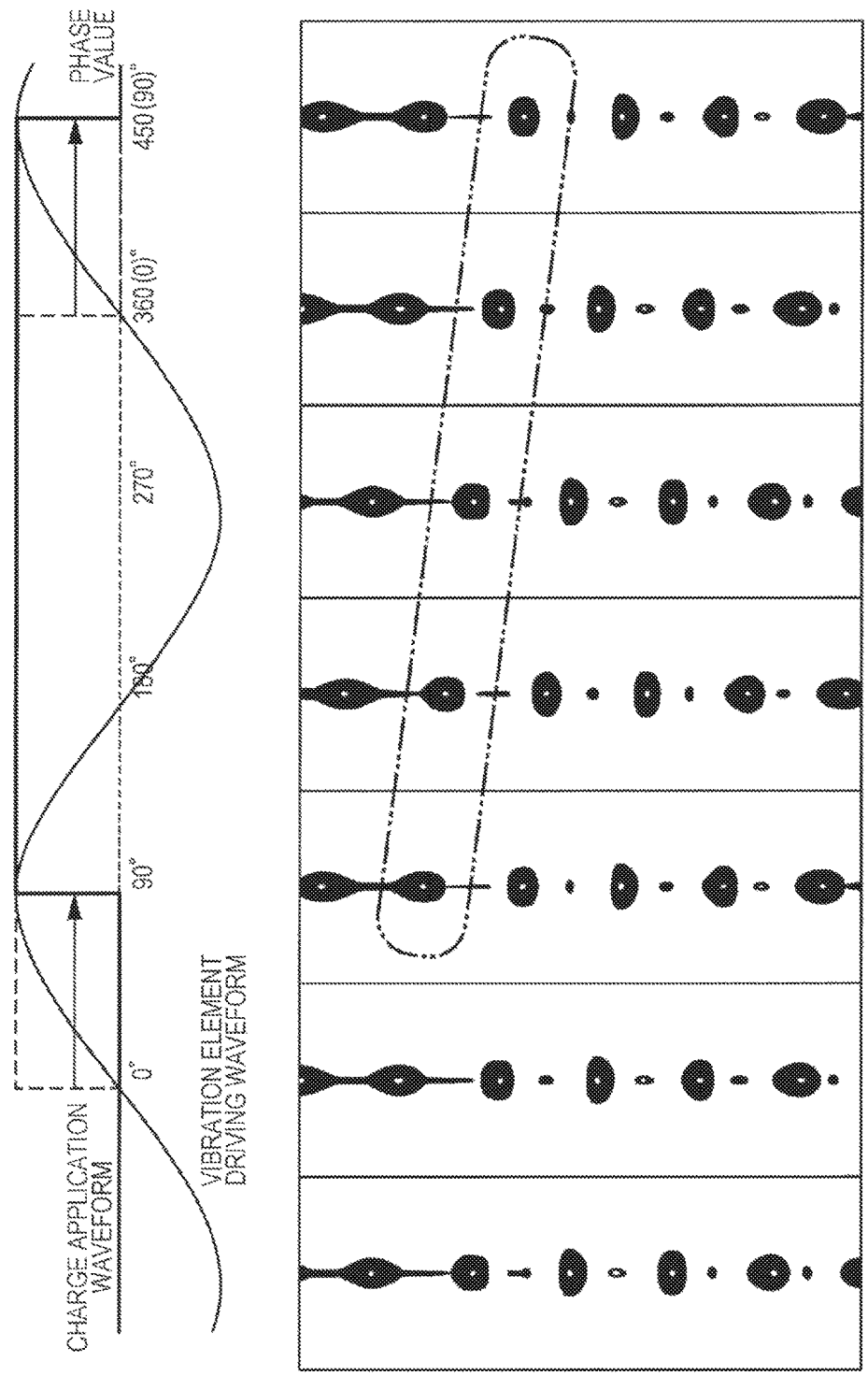

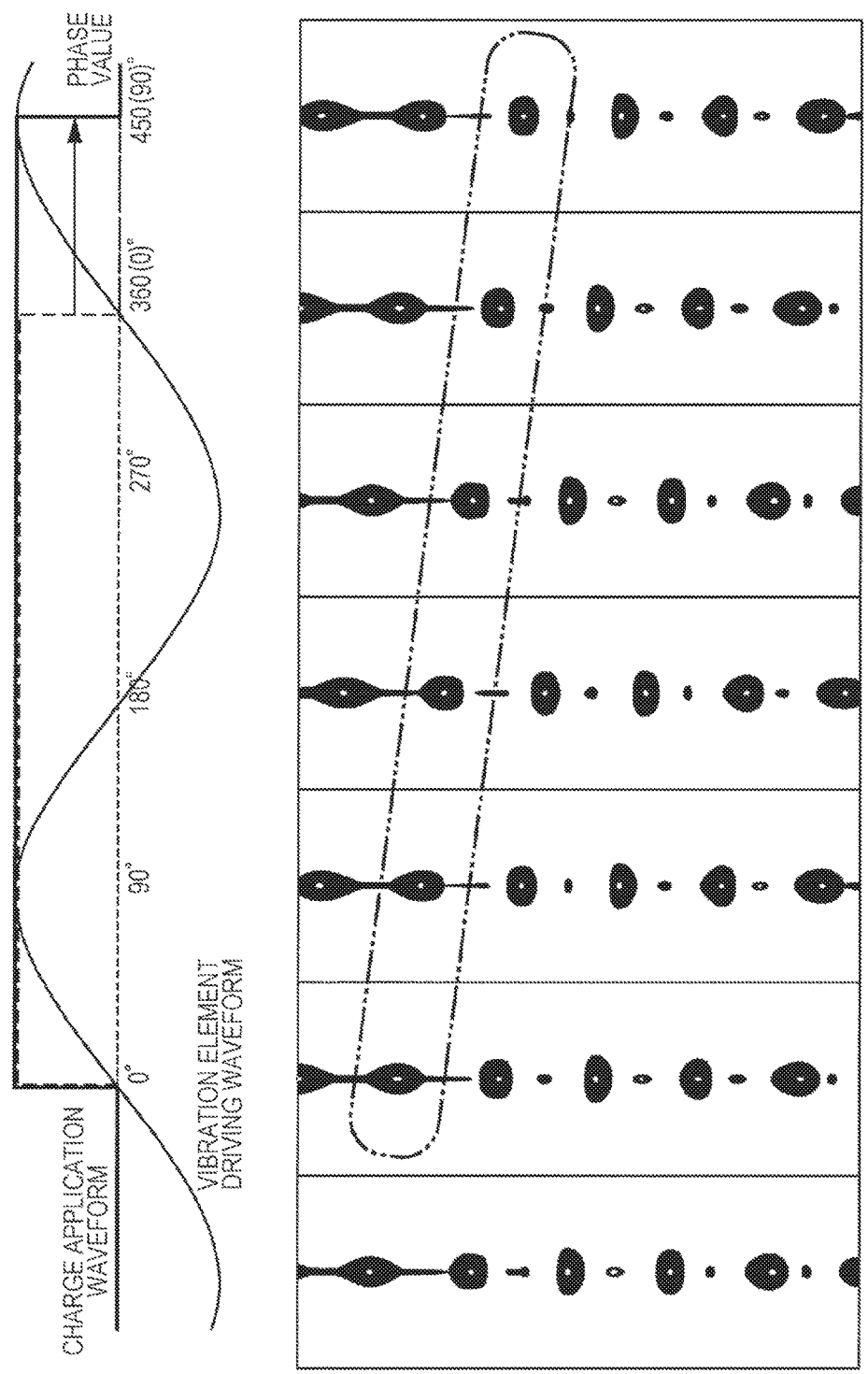
[Fig. 6]

[Fig. 7]
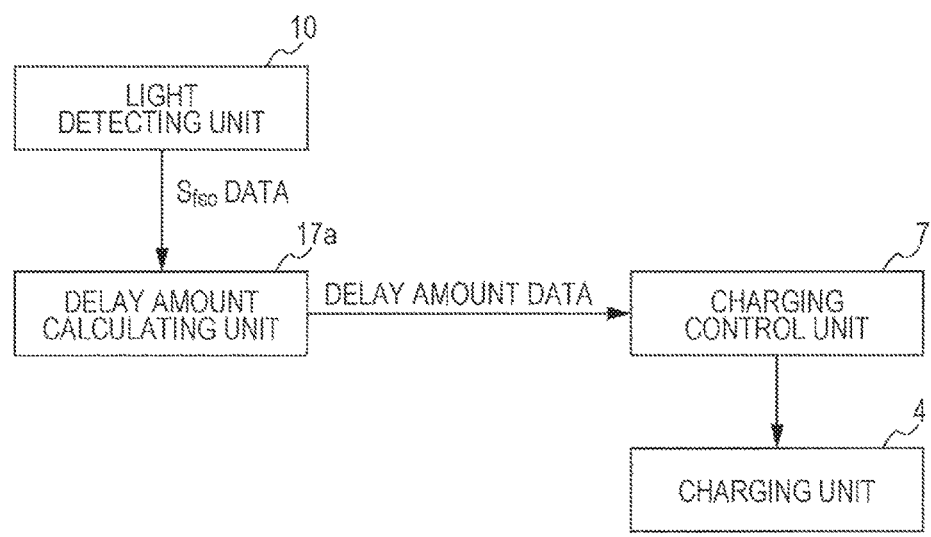

[Fig. 8]
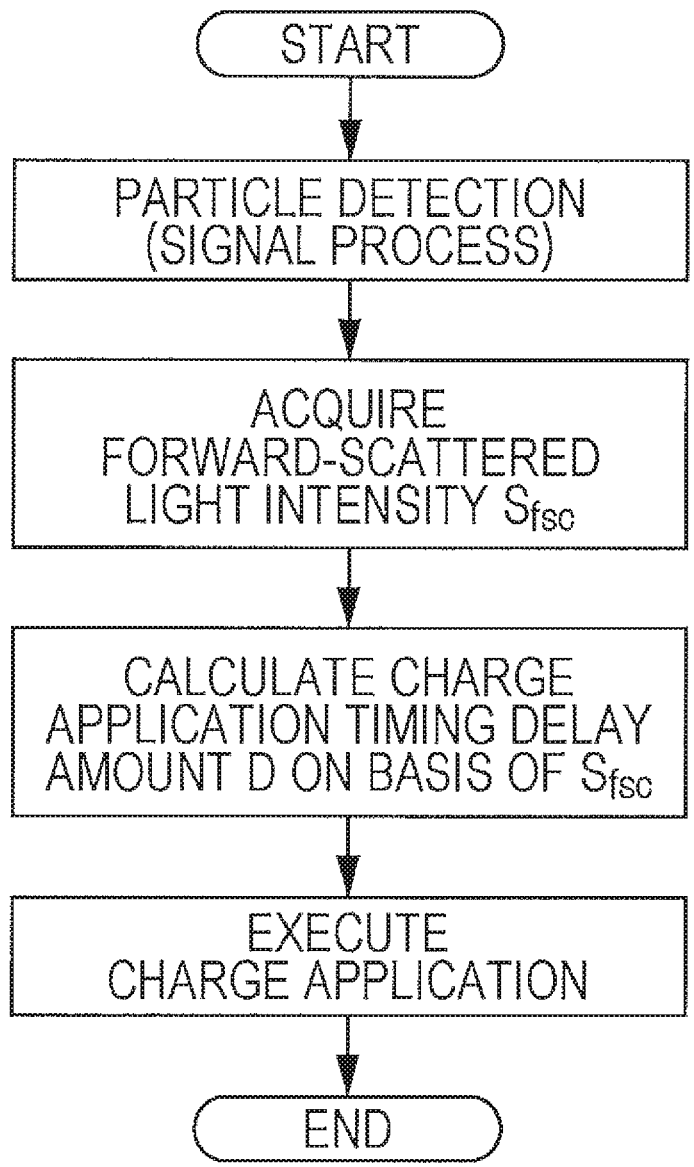

[Fig. 9]
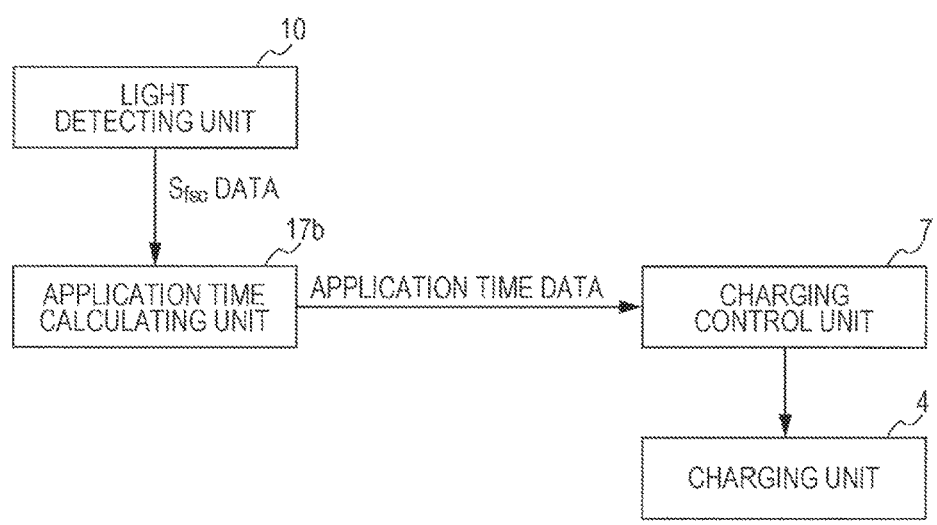

[Fig. 10]
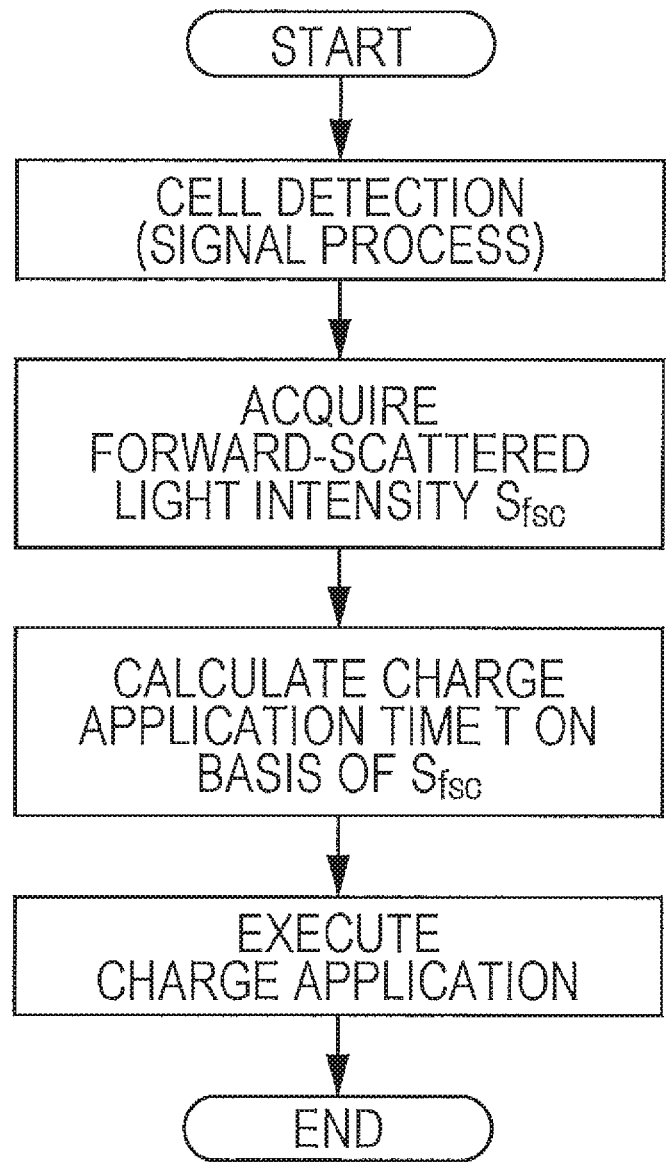

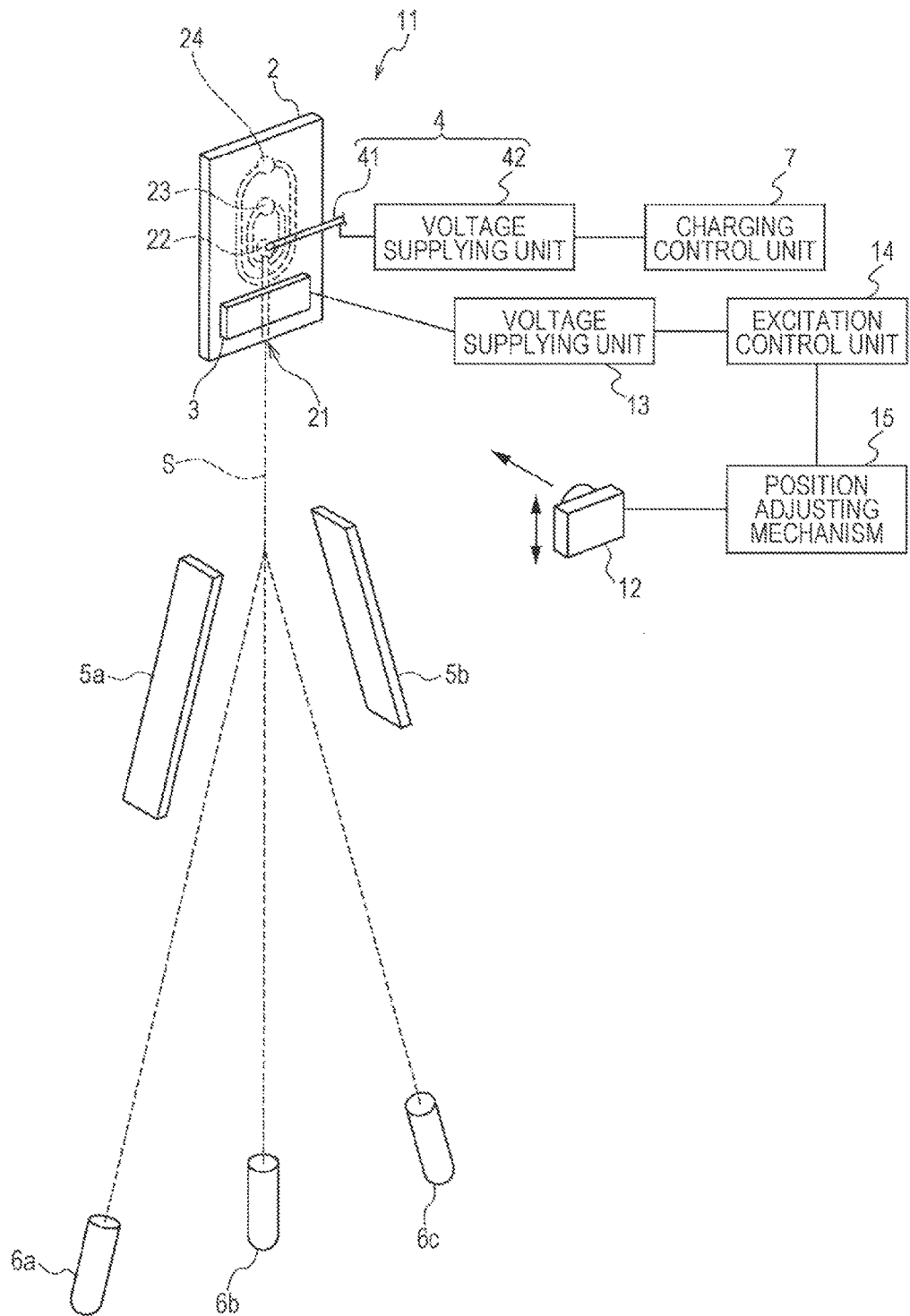
[Fig. 11]

[Fig. 12]
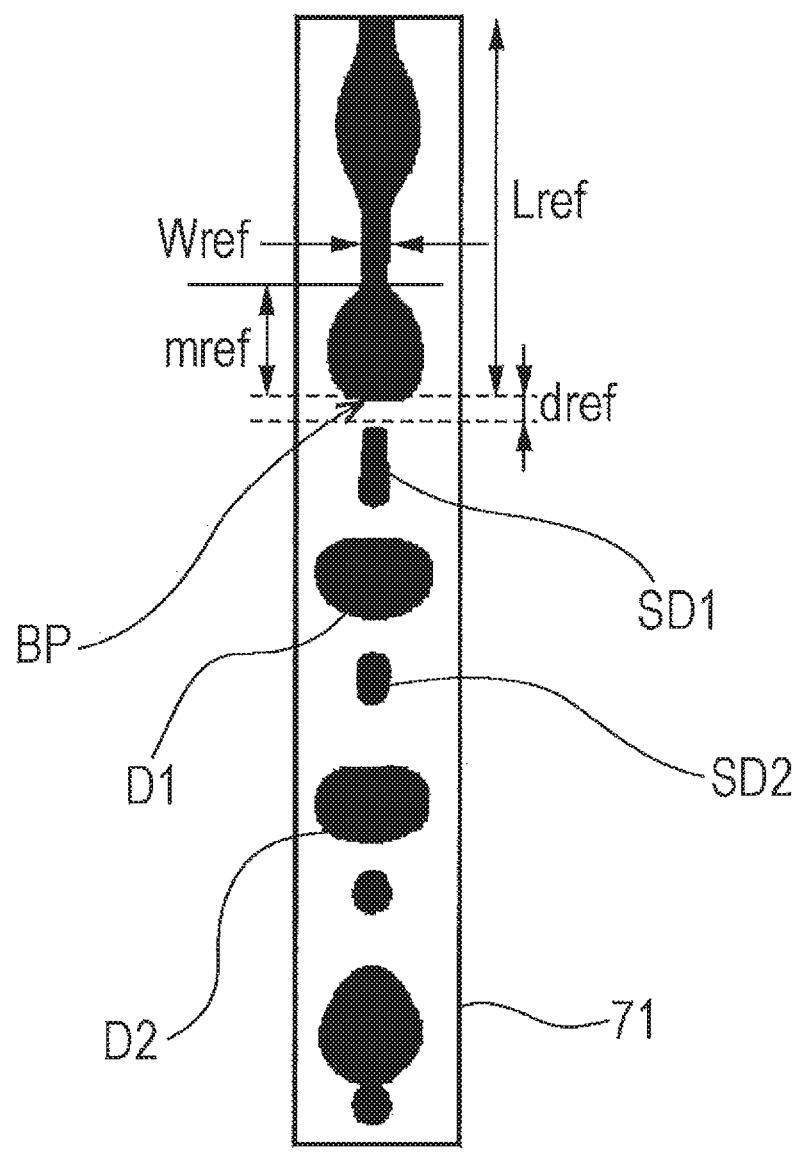

[Fig. 13]
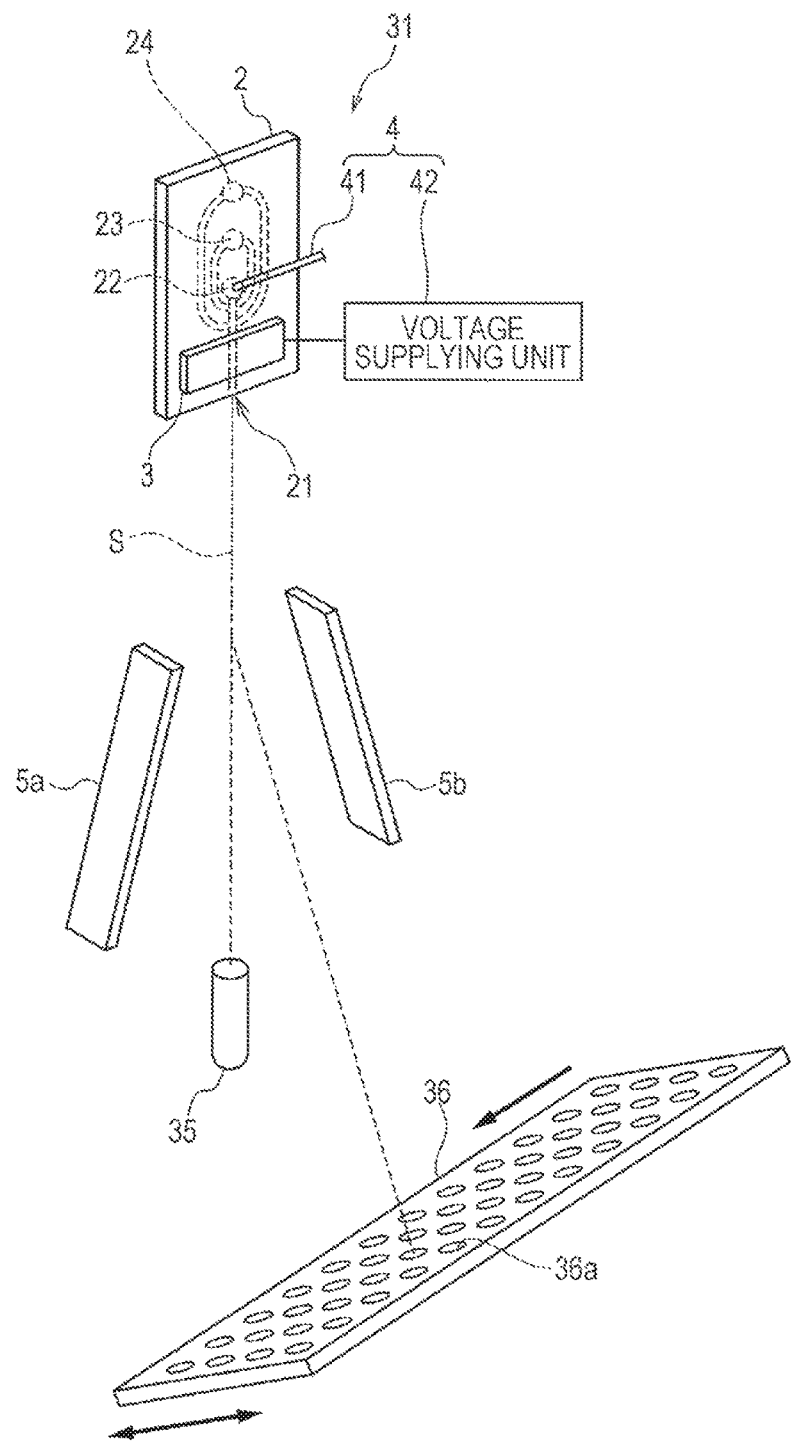

[Fig. 14]
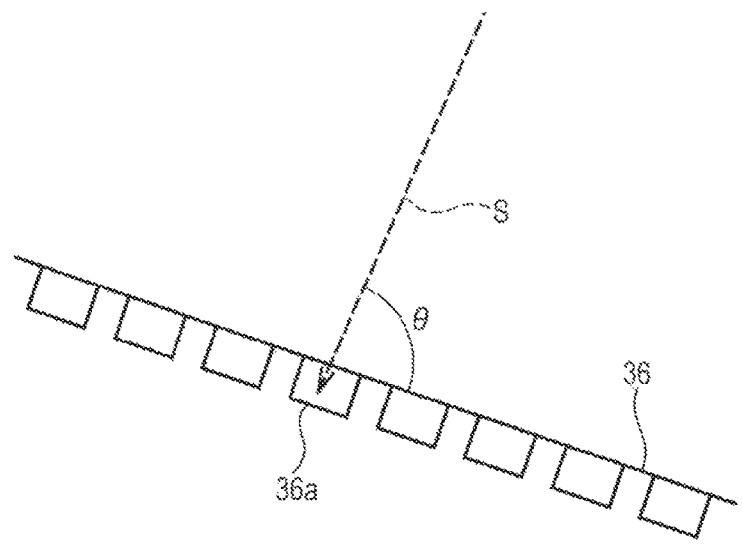
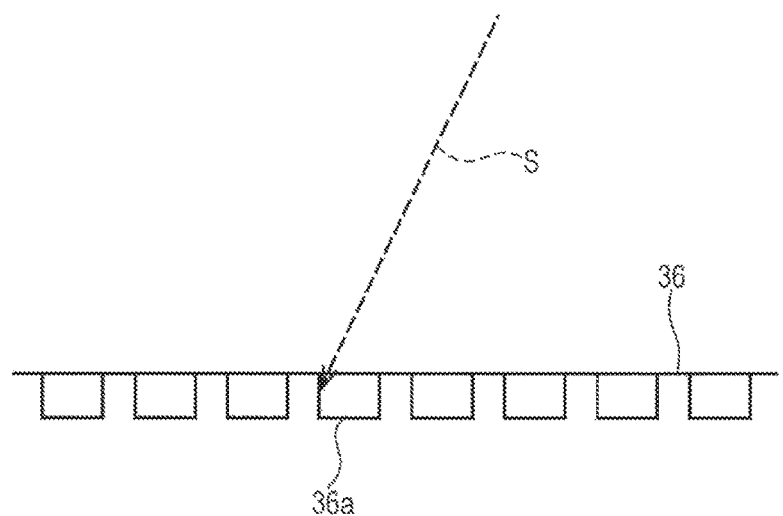

[Fig. 15]
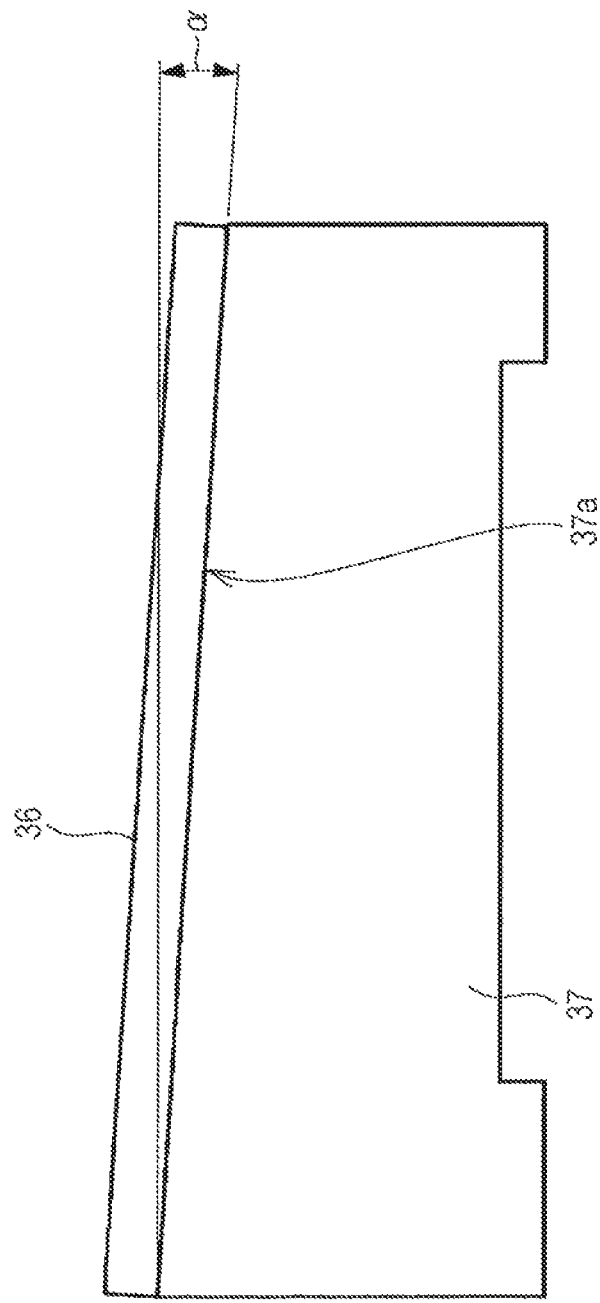

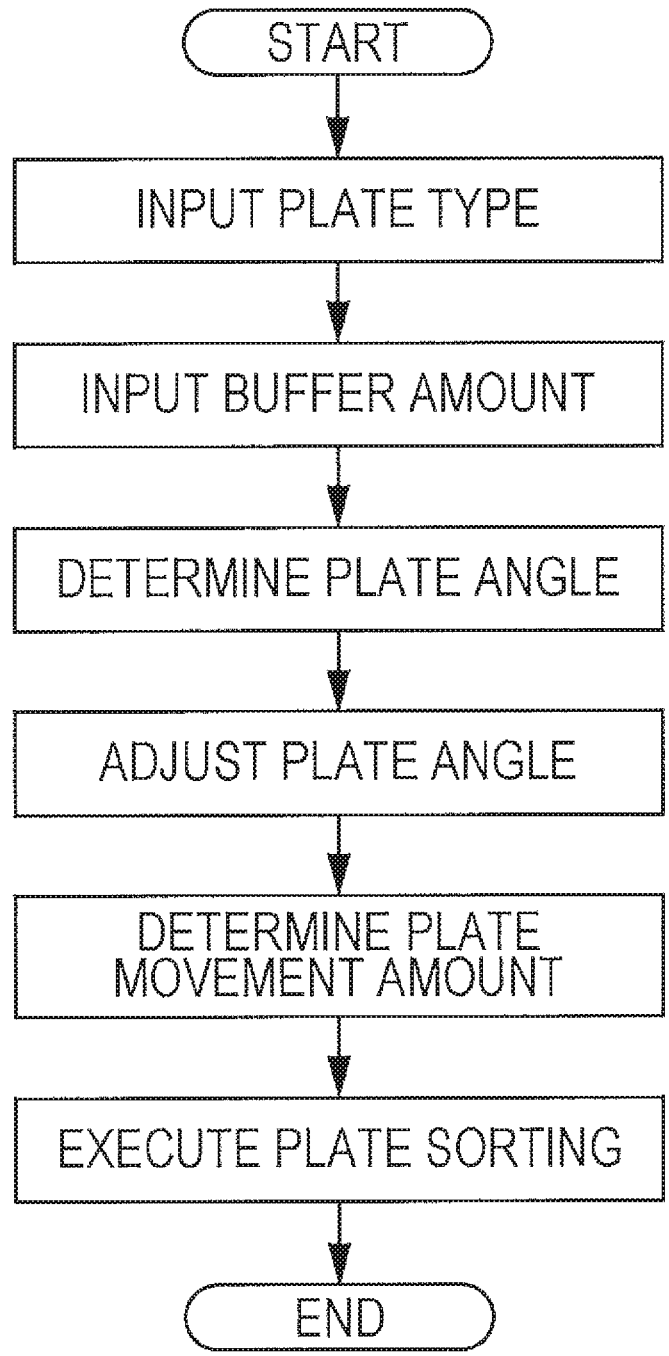
[Fig. 16]

PARTICLE SORTING APPARATUS, PARTICLE SORTING METHOD, AND NON-TRANSITORY COMPUTER-READABLE STORAGE MEDIUM STORING PROGRAM

CROSS REFERENCE TO RELATED APPLICATIONS

This application is a U.S. National Phase of International Patent Application No. PCT/JP2015/000524 filed on Feb. 5, 2015, which claims priority benefit of Japanese Patent Application No. 2014-026620 filed in the Japan Patent Office on Feb. 14, 2014. Each of the above-referenced applications is hereby incorporated herein by reference in its entirety.

TECHNICAL FIELD

The present disclosure relates to a particle sorting apparatus, a particle sorting method, and a non-transitory computer-readable storage medium storing program. In detail, the present disclosure relates to technology for sorting particles on the basis of a result analyzed by an optical method and collecting the particles.

BACKGROUND ART

In the past, an optical measurement method using flow cytometry (a flow cytometer) has been used to analyze living body-related microparticles such as a cell, a microorganism, and a liposome. The flow cytometer is a device that radiates light to microparticles flowing through a flow channel formed in a flow cell or a microchip, detects fluorescent light or scattered light emitted from the individual microparticles, and analyzes the microparticles.

The flow cytometer includes a function of sorting only the microparticles having a specific characteristic, on the basis of an analysis result, and collecting the microparticles. Particularly, a microparticle device sorting cells is referred to as a "cell sorter". Generally, in the cell sorter, vibration is applied to a flow cell or a microchip by a vibration element to make a fluid discharged from a flow channel become liquid droplets (refer to PTL 1 and 2).

After positive (+) or negative (−) charges are applied to the liquid droplets separated from the fluid, an advancement direction of the liquid droplets is changed by a deflection plate and the liquid droplets are collected to a predetermined container. In addition, technology for distributing one specific cell to each reaction portion of a base material used for a polymerase chain reaction (PCR) method, using the sorting function by the cell sorter, is also suggested in the past (refer to PTL 3).

CITATION LIST

Patent Literature

[PTL 1] JP 2007-532874 W
[PTL 2] JP 2010-190680 A
[PTL 3] JP 2010-510782 W

SUMMARY

According to some embodiments, a particle sorting apparatus comprises a charging unit configured to apply charges to at least a portion of liquid droplets ejected from an orifice, and a charging control unit configured to adjust a charge application end time for the applied charges according to sizes of particles included in the liquid droplets. In some embodiments, a particle sorting method comprises applying charges to at least a portion of liquid droplets ejected from an orifice, and adjusting a charge application end time according to sizes of particles included in the liquid droplets.

Embodiments also include a non-transitory computer-readable storage medium storing machine-readable instructions for causing a charging control unit of a particle sorting apparatus to execute a function of adjusting a charge application end time according to sizes of particles detected in liquid droplets that are ejected from an orifice.

Technical Problem

However, in the particle sorting apparatus according to the related art such as the cell sorter, when particles having different sizes are mixed in a sample liquid, an advancement direction of the liquid droplets becomes unstable, the particles are not distributed to the predetermined container or the reaction portion, and sorting precision or sorting efficiency is deteriorated. For this reason, in the particle sorting apparatus according to the related art, a particle size enabling stable sorting is set to become equal to or less than ⅕ of an orifice diameter. In this case, however, it is necessary to increase the orifice diameter according to sizes of sorting object particles and a sorting rate decreases.

Therefore, it is desirable to provide a particle sorting apparatus, a particle sorting method, and a non-transitory computer-readable storage medium storing program enabling sorting object particles to be sorted with high precision, even when the sorting object particles are large.

Solution to Problem

As a result obtained by zealously performing experiments and examinations to solve the above-described problems, the present inventors have found that break-off timing at which a fluid discharged from an orifice is made to become liquid droplets tends to delay, when large cells or particles exist in the liquid droplets. If the break-off timing is deviated, appropriate charges are not applied to the liquid droplets. For this reason, the liquid droplets having the large cells drop more inward than the liquid droplets charged appropriately. That is, if the particles having the large sizes are included in the sorting object particles, the break-off timing becomes unstable. As a result, an angle of a side stream is not stabilized and splashes are generated in the sorting object liquid droplets.

Therefore, in the present disclosure, a charge application end time is adjusted according to the delay of the break-off timing occurring when the particles having the large sizes are sorted. Thereby, the charges can applied stably to the liquid droplets including the particles having the large sizes and generation of the splashes can be decreased.

That is, a particle sorting apparatus according to an embodiment of the present disclosure includes a charging unit that applies charges to at least a part of liquid droplets ejected from an orifice to generate a fluid stream and a charging control unit that adjusts a charge application end time in the charging unit according to sizes of particles included in the liquid droplets.

The charging control unit changes a start time of a charge application waveform according to the sizes of the particles included in the liquid droplets.

In some embodiments, the charging control unit changes a charge application duration according to the sizes of the particles included in the liquid droplets.

The particle sorting apparatus according to the embodiment of the present disclosure may further include a forward-scattered light detecting unit that radiates light to particles flowing through a flow channel and detects forward-scattered light generated from the particles by the light radiation. In this case, the charging control unit adjusts the charge application end time, on the basis of a detection result of the forward-scattered light detecting unit.

When intensity of the forward-scattered light detected by the forward-scattered light detecting unit is equal to or more than a preset threshold value, the charging control unit may control the charging unit such that the start time of the charge application waveform is delayed as compared with when the intensity of the forward-scattered light is less than the threshold value.

The particle sorting apparatus according to the embodiment of the present disclosure may further include a delay amount calculating unit that calculates a delay amount of the charge application waveform on the basis of intensity of the forward-scattered light detected by the forward-scattered light detecting unit and the charging control unit may control the charging unit such that the charge application waveform is delayed according to the delay amount calculated by the delay amount calculating unit.

Alternatively, when intensity of the forward-scattered light detected by the forward-scattered light detecting unit is equal to or more than a preset threshold value, the charging control unit may control the charging unit such that a charge application duration is lengthened as compared with when the intensity of the forward-scattered light is less than the threshold value.

The particle sorting apparatus according to the embodiment of the present disclosure may further include an application time calculating unit that calculates a charge application duration on the basis of intensity of the forward-scattered light detected by the forward-scattered light detecting unit and the charging control unit may control the charging unit such that the charges are applied for the charge application duration calculated by the application time calculating unit.

Meanwhile, in the particle sorting apparatus according to the embodiment of the present disclosure, the orifice may be formed in an exchangeable microchip and the charging unit may include a charging electrode arranged to contact a sheath liquid and/or a sample liquid flowing through a flow channel provided in the microchip.

Alternatively, the orifice may be formed in a flow cell.

A particle sorting method according to an embodiment of the present disclosure includes applying charges to at least a part of liquid droplets ejected from an orifice to generate a fluid stream and adjusting a charge application end time according to sizes of particles included in the liquid droplets.

A non-transitory computer-readable storage medium storing program according to an embodiment of the present disclosure causes a charging control unit of a particle sorting apparatus to execute a function of adjusting a charge application end time, according to sizes of particles included in liquid droplets ejected from an orifice to generate a fluid stream.

Advantageous Effects of Invention

According to the present disclosure, sorting object particles can be sorted with high precision, even when the sorting object particles are large. The effects described herein are not necessarily limitative and may be any effects described in the present disclosure.

BRIEF DESCRIPTION OF DRAWINGS

FIG. 1 is a diagram schematically illustrating a configuration example of a particle sorting apparatus according to a first embodiment of the present disclosure;

FIG. 2 is a flowchart illustrating a charge application end time adjusting method by a change of a start time of a charge application waveform;

FIG. 3 is a flowchart illustrating a charge application end time adjusting method by a change of a charge application duration;

FIG. 4 is a diagram illustrating a relation of charge application and a liquid droplet formation state in a "normal mode";

FIG. 5 is a diagram illustrating a liquid droplet formation state when a charge application end time is adjusted by a change of a start time of a charge application waveform;

FIG. 6 is a diagram illustrating a liquid droplet formation state when a charge application end time is adjusted by a change of a charge application duration;

FIG. 7 is a block diagram illustrating a configuration example of a charging control mechanism of a particle sorting apparatus according to a first modification of the first embodiment of the present disclosure;

FIG. 8 is a flowchart illustrating a charge application end time adjusting method in the particle sorting apparatus according to the first modification of the first embodiment of the present disclosure;

FIG. 9 is a block diagram illustrating a configuration example of a charging control mechanism of a particle sorting apparatus according to a second modification of the first embodiment of the present disclosure;

FIG. 10 is a flowchart illustrating a charge application end time adjusting method in the particle sorting apparatus according to the second modification of the first embodiment of the present disclosure;

FIG. 11 is a diagram schematically illustrating a configuration example of a particle sorting apparatus according to a second embodiment of the present disclosure;

FIG. 12 is a diagram schematically illustrating an example of an image imaged by a camera 12 illustrated in FIG. 11;

FIG. 13 is a diagram schematically illustrating a configuration example of a particle sorting apparatus according to a third embodiment of the present disclosure;

FIG. 14A is a diagram schematically illustrating a relation of a side stream and a well plate in the particle sorting apparatus illustrated in FIG. 13, and FIG. 14B is a diagram schematically illustrating a relation of a side stream and a well plate in a particle sorting apparatus according to the related art;

FIG. 15 is a lateral view schematically illustrating a state when a well plate is placed on a plate holder in which a plate placing unit is inclined; and FIG. 16 is a flowchart illustrating an operation example of the particle sorting apparatus illustrated in FIG. 13.

DESCRIPTION OF EMBODIMENTS

Hereinafter, embodiments to carry out the present disclosure will be described in detail with reference to the accompanying drawings. The present disclosure is not limited to each embodiment described below. The following description will be given in the following order.

1. First embodiment (example of particle sorting apparatus adjusting charge application end time according to size of particle)
2. First modification of first embodiment (example of particle sorting apparatus including delay amount calculating unit)
3. Second modification of first embodiment (example of particle sorting apparatus including application time calculating unit)
4. Second embodiment (example of particle sorting apparatus adjusting charge application end time and controlling vibration element on basis of imaged liquid droplet image)
5. Third embodiment (example of particle sorting apparatus in which plate for liquid droplet collection is obliquely arranged)

1. First Embodiment

First, a particle sorting apparatus according to a first embodiment of the present disclosure will be described. FIG. 1 is a diagram illustrating a schematic configuration of the particle sorting apparatus according to the first embodiment of the present disclosure.

<Entire Configuration of Apparatus>

A particle sorting apparatus 1 according to this embodiment sorts particles on the basis of a result analyzed by an optical method and collects the particles. As illustrated in FIG. 1, the particle sorting apparatus 1 includes a microchip 2, a vibration element 3, a charging unit 4, a charging control unit 7, and deflection plates 5a and 5b.

<With Respect to Particle>

In the particles that are analyzed and sorted by the particle sorting apparatus 1 according to this embodiment, living body-related microparticles such as a cell, a microorganism, and a ribosome or synthetic particles such as a latex particle, a gel particle, and an industrial particle are included widely.

Chromosomes, ribosome, mitochondria, and organelles constituting various cells are included in living body-related microparticles. In addition, plant cells, animal cells, and blood cells are included in the cells. In addition, bacteria such as colon bacilli, viruses such as tobacco mosaic viruses, and fungi such as yeasts are included in microorganisms. In addition, living body-related macromolecules such as nucleic acids, proteins, and complexes thereof can be included in the living body-related microparticles.

Meanwhile, particles formed of an organic polymer material, an inorganic material, or a metal material are exemplified as the industrial particles. As the organic polymer material, polystyrene, styrene divinylbenzene, and polymethylmethacrylate can be used. In addition, glass, silica, and a magnetic material can be used as the inorganic material. As the metal material, colloidal gold and aluminum can be used. The shape of these particles is generally a spherical shape. However, the shape may be a nonspherical shape and a size and a mass are also not limited.

<Microchip 2>

In the microchip 2, a sample inlet 22 into which a liquid (sample liquid) including sorting object particles is introduced, a sheath inlet 23 into which a sheath liquid is introduced, and a suction outlet 24 to remove clogging or bubbles are formed. In the microchip 2, the sample liquid is introduced into the sample inlet 22, joins with the sheath liquid introduced into the sheath inlet 23, is sent to a sample flow channel, and is ejected from an orifice 21 provided in a termination of the sample flow channel.

In addition, a suction flow channel communicating with the suction outlet 24 is connected to the sample flow channel. The suction flow channel makes a pressure in the sample flow channel become a negative pressure, makes the flow backward temporarily, and removes the clogging or the bubbles, when the clogging or the bubbles are generated in the sample flow channel. A negative pressure source such as a vacuum pump is connected to the suction outlet 24.

The microchip 2 can be formed of glass or various plastics (PP, PC, COP, and PDMS). Because the microchip 2 has permeability for measurement light radiated from a light detecting unit to be described below, has small autofluorescence, and small wavelength dispersion, a material of the microchip is preferably a material having small optical error.

Formation of the microchip 2 can be performed by wet etching or dry etching of a glass substrate and nanoimprinting, injection molding, and mechanical processing of a plastic substrate. The microchip 2 can be formed by sealing a substrate provided with the sample flow channel with a substrate made of the same material or a different material.

<Vibration Element 3>

The vibration element 3 applies minute vibration to a liquid flowing through the flow channel, makes a fluid discharged from the orifice 21 become liquid droplets, and generates a fluid stream (flow of the liquid droplets) S. As the vibration element 3, a piezoelectric element can be used. The vibration element 3 may be provided at a position where vibration can be applied to the liquid flowing through the flow channel, may be arranged in the microchip 2, may be arranged to contact the microchip 2, and may be attached to piping such as sheath piping to introduce a liquid into the flow channel.

<Charging Unit 4>

The charging unit 4 applies positive or negative charges to the liquid droplet ejected from the orifice 21 and includes a charging electrode 41 and a voltage source (voltage supplying unit 42) to apply a predetermined voltage to the charging electrode 41. The charging electrode 41 is arranged to contact the sheath liquid and/or the sample liquid flowing through the flow channel and applies the charges to the sheath liquid and/or the sample liquid. For example, the charging electrode 41 is inserted into a charging electrode inlet of the microchip 2.

In FIG. 1, the charging electrode 41 is arranged to contact the sample liquid. However, the present disclosure is not limited thereto and the charging electrode 41 may be arranged to contact the sheath liquid and may be arranged to contact both the sheath liquid and the sample liquid. However, if an influence on sorting object cells is considered, the charging electrode 41 is preferably arranged to contact the sheath liquid.

As such, the positive or negative charges are applied to the desired liquid droplets to charge the desired liquid droplets, so that the liquid droplets including any particles can be separated by the electric force. In addition, charging timing by the charging unit 4 and a voltage supplied to the vibration element 3 are synchronized, so that only any liquid droplets can be charged.

<Deflection Plates 5a and 5b>

The deflection plates 5a and 5b change an advancement direction of each liquid droplet in the fluid stream S by the electric force acting between the charges applied to the liquid droplets and the deflection plates and guide the liquid droplets to predetermined collection containers 6a to 6c. The deflection plates 5a and 5b are arranged with the fluid stream S therebetween. For example, generally used electrodes can be used in the deflection plates 5a and 5b.

A positive or negative different voltage is applied to each of the deflection plates 5a and 5b. If the charged liquid droplets pass through the field generated by the voltage application, the electric force (Coulomb force) is generated and each liquid droplet is drawn in a direction of any one of the deflection plates 5a and 5b. In the particle sorting apparatus 1, a direction of the flow (side stream) of the liquid droplet drawn by the field can be controlled by changing the polarity or the amount of charges applied to the liquid droplets. Therefore, a plurality of different particles can be sorted at the same time.

<Collection Containers 6a to 6c>

The collection containers 6a to 6c collect the liquid droplets having passed through a space between the deflection plates 5a and 5b and experimental and versatile plastic tubes or glass tubes can be used as the collection containers. The collection containers 6a to 6c are preferably arranged to be exchangeable in the apparatus. In addition, a liquid discharge flow channel of the collected liquid droplets may be connected to the collection container receiving the particles other than the sorting object particles, among the collection containers 6a to 6c.

The number or type of collection containers arranged in the particle sorting apparatus 1 is not limited in particular. For example, when four or more collection containers are arranged, each liquid droplet may be guided to any collection container according to presence or absence of the electric force acting between the deflection plates 5a and 5b and the liquid droplet and the magnitude thereof and may be collected to the collection container. In addition, instead of using the collection containers 6a to 6c, a base material provided with a plurality of reaction portions (wells) may be used and one specific particle may be distributed to each reaction portion.

<Charging Control Unit 7>

The charging control unit 7 adjusts a charge application end time in the charging unit 4 according to the sizes of the particles included in the liquid droplets. A method of determining the sizes of the particles is not limited in particular. For example, the sizes of the particles can be determined on the basis of a detection result of forward-scattered light measured by a light detecting unit to be described below. In this case, the charging control unit 7 changes a charge application start time of a charge application waveform or a changes a charge application duration according to whether intensity of the forward-scattered light detected by the light detecting unit is equal to or more than a specific value (threshold value) and adjusts a charge application end time.

Specifically, when the intensity of the forward-scattered light is equal to or more than a preset threshold value, the charging control unit 7 may control the charging unit 4, such that the charge application waveform is delayed or the charge application duration is increased as compared with when the intensity of the forward-scattered light is less than the threshold value. Thereby, even though the sorting object particles are large, the charges can be applied at appropriate timing. Therefore, the liquid droplets can be stably guided by the deflection plates 5a and 5b.

<Light Detecting Unit>

In addition, in the particle sorting apparatus 1 according to this embodiment, a light detecting unit (not illustrated in the drawings) that radiates light (excitation light) to a predetermined portion of the sample flow channel and detects light (measurement object light) generated from the particles flowing through the sample flow channel is provided. The light detecting unit can have the same configuration as that of the flow cytometry according to the related art. Specifically, the light detecting unit is configured by a laser light source, a radiation system including a condensing lens, a dichroic mirror, and a band pass filter condensing/radiating laser light for the particles, and a detection system detecting the measurement object light generated from the particles by radiating the laser light.

The detection system is configured by a photo multiplier tube (PMT) and an area imaging element such as a CCD or a CMOS element. The radiation system and the detection system may be configured by the same optical path and may be configured by individual optical paths. The measurement object light detected by the detection system of the light detecting unit is light that is generated from the particles by radiating the excitation light. For example, the measurement object light can be forward-scattered light, side-scattered light, various scattered light such as Rayleigh scattering or Mie scattering, or fluorescent light.

In the measurement object light, the intensity of the forward-scattered light changes in proportion to a surface area of a cell and the forward-scattered light becomes an index to evaluate sizes of the particles. For this reason, the particle sorting apparatus 1 according to this embodiment preferably includes a forward-scattered light detecting unit that detects the forward-scattered light. Thereby, the particle sorting apparatus 1 can easily perform adjustment of a charge application end time by the charging control unit 7.

<Others>

The particle sorting apparatus 1 according to this embodiment may include a pneumatic pressurizing device such as a compressor and a pneumatic detector such as a pressure sensor to supply a stable air pressure to each of the sheath liquid and the sample liquid, in addition to the individual units described above. Thereby, the sheath flow and the sample flow may be stably formed and stabilized liquid droplet formation can be realized.

<Operation>

Next, an operation of the particle sorting apparatus 1 according to this embodiment, that is, a method of sorting the particles using the particle sorting apparatus 1 will be described using the case in which a charging amount is adjusted using a detection result of the forward-scattered light as an example.

When the particles are sorted by the particle sorting apparatus 1 according to this embodiment, the sample liquid including the sorting object particles is introduced into the sample inlet 22 and the sheath liquid is introduced into the sheath inlet 23. In addition, a transmission rate (flow rate) of the particles and an interval of the particles are detected by the light detecting unit at the same time as detection of an optical characteristic of the particles. The detected optical characteristic, flow rate, and interval of the particles are converted into electric signals and the electric signals are output to a whole control unit (not illustrated in the drawings) of the apparatus.

A laminar flow of the sample liquid and the sheath liquid having passed through a light radiating unit in the sample flow channel is discharged from the orifice 21 to a space outside the microchip 2. At this time, vibration is applied to a liquid such as the sheath liquid flowing through the flow channel by the vibration element 3 and the fluid discharged from the orifice 21 is made to become the liquid droplets. In addition, an advancement direction of each liquid droplet is changed by the deflection plates 5a and 5b, on the basis of a detection result in the light detecting unit, and each liquid droplet is guided to the predetermined collection containers 6a to 6c and is collected to the collection containers.

At this time, in the particle sorting apparatus 1 according to this embodiment, the charge application end time in the charging unit 4 is adjusted according to the sizes of the particles included in the liquid droplets. FIG. 2 is a flowchart illustrating a charge application end time adjusting method by a change of start time of a charge application waveform and FIG. 3 is a flowchart illustrating a charge application end time adjusting method by a change of a charge application duration. In addition, FIG. 4 is a diagram illustrating a relation of charge application and a liquid droplet formation state in a "normal mode". In addition, FIG. 5 is a diagram illustrating a liquid droplet formation state when a charge application end time is adjusted by a change of a start time of a charge application waveform and FIG. 6 is a diagram illustrating a liquid droplet formation state when a charge application end time is adjusted by a change of a charge application duration.

The charging control unit 7 can adjust the charge application end time for the liquid droplets including each particle, on the basis of the strength $S_{fsc}$ of the forward-scattered light. Specifically, the charge application end time can be automatically adjusted by performing control to change the start time of a charge application waveform or the charge application duration, for the particles in which the intensity of the forward-scattered light is equal to or more than a preset threshold value.

For example, when the charge application end time is adjusted by changing the start time of the charge application waveform, as illustrated in FIG. 2, each particle flowing through the flow channel is detected and the intensity (Sfsc) of the forward-scattered light thereof is acquired. In addition, when the intensity of the forward-scattered light of the particles is less than a threshold value (Tfsc), the charges are applied at the normal timing illustrated in FIG. 4 and when the intensity of the forward-scattered light is equal to or more than the threshold value (Tfsc), the charges are applied at timing slower than the normal timing illustrated in FIG. 5.

That is, when the intensity (Sfsc) of the forward-scattered light is equal to or more than the preset threshold value (Tfsc), the charging control unit 7 controls the charging unit 4 such that the charge application waveform is delayed as compared with when the intensity (Sfsc) of the forward-scattered light is less than the threshold value (Tfsc). Here, a delay amount of the charge application waveform can be appropriately selected on the basis of assumed particle sizes and may be set previously.

For example, even when the charge application end time is adjusted by changing the charge application end time, as illustrated in FIG. 3, each particle flowing through the flow channel is detected and the intensity (Sfsc) of the forward-scattered light thereof is acquired. In addition, when the intensity of the forward-scattered light of the particles is less than a threshold value (Tfsc), the charges are applied for the normal time illustrated in FIG. 4 and when the intensity of the forward-scattered light is equal to or more than the threshold value (Tfsc), the charges are applied for a time longer than the normal time illustrated in FIG. 6.

That is, when the intensity (Sfsc) of the forward-scattered light is equal to or more than the preset threshold value (Tfsc), the charging control unit 7 controls the charging unit 4 such that the charge application duration is lengthened as compared with when the intensity (Sfsc) of the forward-scattered light is less than the threshold value (Tfsc). Here, an extension time of the charge application can be appropriately selected on the basis of assumed particle sizes and may be set previously.

As such, the charge application waveform is delayed or the charge application duration is lengthened for the liquid droplets including the particles having the large sizes, so that the charges can be surely applied to the liquid droplets in which break-off timing has been delayed. The "normal charge application waveform" and the "normal charge application duration" described above are determined at the time of adjusting amplitude (a drive value) supplied to the vibration element 3 before measurement, such that a most stabilized side stream is obtained. At this time, according to a relation of a charge application waveform and liquid droplet formation, the charge application end timing is set as timing immediately after the liquid droplet breaks off, which is a "normal mode".

Meanwhile, it is important to apply the charges until a point of time immediately after the liquid droplet breaks off to stabilize sorting of the particles having the large sizes. When the two charge application end time adjusting methods described above are compared with each other, according to the method of increasing the charge application duration, a margin is left in the charge application duration and the charge application duration is increased, so that the charges can be surely applied to the liquid droplets, regardless of the change in the break-off timing. However, according to this method, when the variation in the break-off timing is large, the amount of charges applied to each liquid droplet may be changed.

Meanwhile, according to the method of delaying the charge application waveform, because the charge application duration does not change and the total amount of charges applied to each liquid droplet becomes constant, the change in the amount of charges is not generated. In the method of delaying the charge application waveform, if the delay amount of the break-off timing can be estimated with high precision using a method to be described below, the charge application waveform is delayed according to the delay amount, so that sorting can be stabilized while the charging amount of each liquid droplet is constantly maintained.

In addition, the adjustment of the charge application end time can be automatically executed by creating a program to realize a function of changing the start time of the charge application waveform or the charge application duration according to the sizes of the particles included in the liquid droplets and mounting the program on the charging control unit 7 of the particle sorting apparatus 1. Alternatively, according to necessity, a user can select a "normal mode" and a "large-diameter particle mode" and execute the selected modes.

As described in detail above, in the particle sorting apparatus according to this embodiment, because the charge application end time in the charging unit is adjusted according to the sizes of the particles included in the liquid droplets, the charges can be stably applied to the liquid droplets including the particles having the large size. Thereby, even when the sorting object particles are large, disturbance of the side stream due to the delay of the break-off timing can be alleviated and the particles can be sorted with high precision.

As a result, in the sorting apparatus according to the related art, when the large particles are sorted, an orifice diameter should be increased. However, according to the present disclosure, because it is not necessary to increase the orifice diameter for the particles having the large size, the particles can be sorted at a high speed as compared with the related art.

In the first embodiment described above, the example of the case in which the microchip 2 is used has been described. However, the present disclosure is not limited thereto. Even when a flow cell is used, instead of the microchip 2, the same effect is obtained.

2. First Modification of First Embodiment

Next, a particle sorting apparatus according to a first modification of the first embodiment of the present disclosure will be described. FIG. 7 is a block diagram illustrating a configuration example of a charging control mechanism of the particle sorting apparatus according to this modification and FIG. 8 is a flowchart illustrating a charge application end time adjusting method thereof.

<Apparatus Configuration>

Because the intensity Sfsc of the forward-scattered light becomes a value approximately proportional to a surface area (size) of particles, stability of sorting can be further improved by setting a delay amount of charge application waveform on the basis of the intensity Sfsc of the forward-scattered light of each particle. Therefore, the particle sorting apparatus according to this modification includes a delay amount calculating unit 9 that calculates a delay amount D of the charge application waveform, on the basis of the intensity Sfsc of the forward-scattered light detected by a light detecting unit 8, as illustrated in FIG. 7.

<Operation>

In the particle sorting apparatus according to this modification, a charging unit 4 is controlled by a charging control unit 7, such that the charge application waveform is delayed according to the delay amount D calculated by the delay amount calculating unit 9. Specifically, as illustrated in FIG. 8, first, particles are detected in the light detecting unit 8 and the intensity Sfsc of the forward-scattered light thereof is acquired. In addition, the delay amount D of the charge application waveform is calculated in the delay amount calculating unit 9, on the basis of data of the intensity Sfsc of the forward-scattered light. The data of the delay amount D is transmitted to the charging control unit 7 and is used for control of the charge application by the charging unit 4.

As such, in the particle sorting apparatus according to this modification, the delay amount D of the charge application waveform is calculated from the intensity Sfsc of the forward-scattered light and the charging control unit 7 controls the charge application waveform by the charging unit 4 on the basis of a value of the delay amount. Therefore, sorting stability can be further improved.

The other configuration and effect in the particle sorting apparatus according to this modification are the same as those in the first embodiment described above.

3. Second Modification of First Embodiment

Next, a particle sorting apparatus according to a second modification of the first embodiment of the present disclosure will be described. FIG. 9 is a block diagram illustrating a configuration example of a charging control mechanism of the particle sorting apparatus according to this modification and FIG. 10 is a flowchart illustrating a charge application end time adjusting method thereof.

<Apparatus Configuration>

As described above, because the intensity Sfsc of the forward-scattered light becomes a value approximately proportional to a surface area (size) of particles, stability of sorting can be further improved by setting a charge application duration on the basis of the intensity Sfsc of the forward-scattered light of each particle. Therefore, the particle sorting apparatus according to this modification includes an application time calculating unit 10 that calculates a charge application duration T, on the basis of the intensity Sfsc of the forward-scattered light detected by a light detecting unit 8, as illustrated in FIG. 9.

<Operation>

In the particle sorting apparatus, a charging control unit 7 controls a charging unit 4, such that the charges are applied to liquid droplets for a time T calculated by the application time calculating unit 10. Specifically, as illustrated in FIG. 10, first, particles are detected in the light detecting unit 8 and the intensity $S_{fsc}$ of the forward-scattered light thereof is acquired. In addition, the charge application duration T is calculated in the application time calculating unit 10, on the basis of data of the intensity $S_{fsc}$ of the forward-scattered light thereof. The data of the charge application duration T is transmitted to the charging control unit 7 and is used for control of the charge application by the charging unit 4.

As in the particle sorting apparatus according to this modification, even though the charge application duration T is calculated from the intensity Sfsc of the forward-scattered light and the charging control unit 7 controls the charge application duration by the charging unit 4 on the basis of a value thereof, stability of sorting can be further improved.

The other configuration and effect in the particle sorting apparatus according to this modification are the same as those in the first embodiment described above.

4. Second Embodiment

Next, a particle sorting apparatus according to a second embodiment of the present disclosure will be described. FIG. 11 is a diagram schematically illustrating a configuration example of the particle sorting apparatus according to the second embodiment of the present disclosure. As illustrated in FIG. 11, a particle sorting apparatus 11 according to this embodiment includes an imaging element (camera) 12 to acquire an image of a fluid or a liquid droplet and an excitation control unit 14 to control a driving voltage of a vibration element 3 on the basis of an image imaged by the camera 12, in addition to the configuration of the first embodiment described above.

<Imaging Element (Camera) 12>

The imaging element (camera) 12 images the fluid before becoming the liquid droplet and the liquid droplet, at a position (break-off point BP) where a laminar flow of a sample liquid and a sheath liquid discharged from an orifice 21 becomes the liquid droplet. The fluid and the liquid droplet can be imaged using various imaging elements such as a photoelectric converting element, in addition to an imaging device such as a CCD or a CMOS camera.

In addition, a position adjusting mechanism 15 to change the position of the camera 12 is preferably provided in the camera 12. Thereby, the position of the camera 12 can be easily controlled according to an instruction from the excitation control unit 14 to be described below. In addition, in the particle sorting apparatus 11 according to this embodiment, a light source (not illustrated in the drawings) to illuminate an imaging region may be provided in addition to the camera 12.

<Voltage Supplying Unit 13>

A voltage supplying unit 13 supplies a driving voltage to a vibration element 3. The driving voltage of the vibration element 3 is supplied according to a sine wave to form a stabilized liquid droplet and is controlled by two elements of a frequency (a clock value) and amplitude (a drive value).

<Excitation Control Unit 14>

An excitation control unit 14 controls driving power of the vibration element 3, on the basis of an image imaged by the camera 12, and controls a position of the camera 12 according to necessity. Specifically, the excitation control unit 14 controls the voltage supplying unit 13 or the position adjusting mechanism 15, on the basis of a state of a fluid before forming a liquid droplet in an image or a state of a satellite liquid droplet existing between a break-off point and a liquid droplet closest to the break-off point or both the state of the fluid and the state of the satellite liquid droplet.

The excitation control unit 14 can be configured by an information processing device including a general-purpose processor, a main storage device, and an auxiliary storage device. In this case, the voltage supplying unit 13 or the position adjusting mechanism 15 can be automatically controlled by inputting image data imaged by an imaging element such as the camera 12 to the excitation control unit 14 and executing a programmed control algorithm. Such a computer program may be stored in a recording medium such as a magnetic disk, an optical disk, a magneto-optical disk, and a flash memory or may be distributed through a network.

<Operation>

Next, an operation of the particle sorting apparatus 11 according to this embodiment will be described. In addition to control of a charging unit 4 by a charging control unit 7, the particle sorting apparatus 11 according to this embodiment acquires images of the fluid and the liquid droplet at the break-off point by the camera 12 and controls the vibration element 3 by the excitation control unit 14, on the basis of the images.

(Acquisition of Liquid Droplet Image)

A method of imaging the fluid and the liquid droplet by the imaging element (camera) 12 is not limited in particular. For example, light is emitted from a light source for a constant time for every liquid droplet formation cycle, so that a liquid droplet image of specific timing of liquid droplet formation can be acquired. In addition, light source light emission timing at a liquid droplet formation clock is changed, so that an aspect where a liquid droplet is formed in one cycle can be confirmed. Because a liquid droplet formation frequency is about 10 k to 30 kHz and a frame frequency of the imaging element (camera) 12 is about 30 fps in general, one liquid droplet image is obtained by overlapping hundreds to thousands of liquid droplets.

(Control of Driving Voltage)

When the driving voltage of the vibration element 3 is controlled by the excitation control unit 14, an image (reference image) imaged by adjusting a state of the fluid or the liquid droplet to an optimal state in advance is prepared and the driving voltage is adjusted such that an image at the time of sorting is matched with the reference image. FIG. 12 is a diagram schematically illustrating an example of an image imaged by the camera 12. The comparison of the reference image and the image at the time of sorting can be performed by a distance (first satellite upper portion interval) d from the break-off point BP to a first satellite $SD_1$ and a width (liquid column constriction width) w of a constriction portion in the fluid immediately before becoming the liquid droplets.

The first satellite upper portion interval d, the liquid column constriction width w, and the liquid column length L (position of the break-off point BP) are in a close relation and the liquid column length L, the first satellite upper portion interval d, and the liquid column constriction width w become indexes directly showing stability of the break-off point BP. In addition, the driving voltage of the vibration element 3 is controlled on the basis of a value of the first satellite upper portion interval d or the liquid column constriction width w, so that a liquid droplet shape of the fluid stream S can be stabilized.

For example, the driving voltage of the vibration element 3 is controlled by the excitation control unit 14, such that the first satellite upper portion interval d in the image at the time of sorting becomes the same as a first satellite upper portion interval $d_{ref}$ in a reference image 71 illustrated in FIG. 12. If the driving voltage of the vibration element 3 is increased, a value of the first satellite upper portion interval d increases. In contrast, if the driving voltage of the vibration element 3 is decreased, the value of the first satellite upper portion interval d decreases. Therefore, the excitation control unit 14 can control the driving voltage of the vibration element 3 using the relation.

The first satellite upper portion interval d is sensitive to a change of the liquid droplet shape of the fluid stream S. Therefore, the first satellite upper portion interval d is continuously adjusted to be matched with the first satellite upper portion interval $d_{ref}$ of the reference image 71, so that the liquid droplet shape at the time of sorting can be maintained in a stabilized state, similar to the reference image.

In addition, the driving voltage of the vibration element 3 can be controlled using the liquid column constriction width w, instead of the first satellite upper portion interval dref. In this case, the driving voltage of the vibration element 3 is controlled such that the value of the liquid column constriction width w in the image at the time of sorting becomes equal to the liquid column constriction width wref in the reference image 71 illustrated in FIG. 12. If the driving voltage of the vibration element 3 increases, the value of the liquid column constriction width w decreases and if the driving voltage of the vibration element 3 decreases, the value of the liquid column constriction width w increases. Therefore, the excitation control unit 14 can control the driving voltage of the vibration element 3 using the relation.

The liquid column constriction width w also changes sensitively according to the change in the liquid droplet shape of the fluid stream S, similar to the first satellite upper portion interval dref described above. Therefore, the liquid column constriction width w is continuously adjusted to be matched with the liquid column constriction width wref of the reference image 71, so that the fluid stream S can be maintained in a stabilized state, and the position of the break-off point BP is also stabilized.

In the driving voltage control of the vibration element 3 by the excitation control unit 14, any one of the first satellite upper portion interval d and the liquid column constriction width w can be used as the index. However, both the first satellite upper portion interval d and the liquid column constriction width w are used as the indexes, so that the liquid droplet shape in the fluid stream S can be further stabilized. Alternatively, the driving voltage of the vibration element 3 can be controlled on the basis of only the state of the fluid, without using the state of the satellite liquid droplet.

(Control of Camera Position)

At the time of sorting, if the sheath liquid temperature changes according to the change in the environment temperature, the liquid droplet interval in the fluid stream S is changed by the change in the flow rate according to the viscosity change and a position of the break-off point BP, that is, the liquid column length L changes. Thereby, the number of intra-liquid column liquid droplets FD in an image may change and the break-off point BP may not be stably detected and identified.

Therefore, in the particle sorting apparatus 11 according to this embodiment, the position of the camera 12 can be moved according to the change of the liquid column length L in the image, by the excitation control unit 14, according to necessity. As such, if the position of the camera 12 is made to follow the position change of the break-off point BP, a value of the liquid column length L in the image can be constantly maintained. As a result, because the break-off point BP is stably held at a predetermined position corresponding to a reference image in a sorting image, the number of the intra-liquid column liquid droplets FD can be constantly maintained and a previously adjusted drop delay time can be maintained for a long time.

As the method of constantly maintaining the position of the break-off point BP in the image, a method of changing a cutting position of an image is known in addition to the method of moving the camera 12. For example, the fluid and the liquid droplet are imaged using a camera having a wide angle, an image including the break-off point BP is cut from images, and the image is used for control by the excitation control unit 14. In this case, when the position of the break-off point BP changes, the image cutting position is changed to suppress a value of the liquid column length L from changing. Thereby, control of an imaging position according to the movement of the break-off point BP can be realized.

Because the particle sorting apparatus according to this embodiment performs the adjustment of the charge application end time and the control of the driving voltage of the vibration element based on the state of the fluid stream S, the break-off point BP can be maintained with high precision. Thereby, liquid droplet formation as well as charging to the liquid droplets is stabilized. Therefore, even when sorting object particles are large, the particles can be sorted at a high speed and with high precision.

The other configuration and effect in the particle sorting apparatus according to this embodiment are the same as those of the first embodiment described above.

5. Third Embodiment

Next, a particle sorting apparatus according to a third embodiment of the present disclosure will be described. In a particle sorting apparatus such as a cell sorter, when particles such as cells are sorted, plate sorting using a base material (hereinafter, referred to as a well plate) provided with a plurality of reaction portions (wells) may be performed. Various kinds of wells such as 6 wells, 12 wells, 24 wells, 48 wells, 96 wells, and 384 wells exist in the well plate used for the plate sorting. When the number of wells increases, a diameter of an opening of the well decreases.

For this reason, in the particle sorting apparatus according to the related art, if a plate having a large number of wells is used, it is difficult to distribute targeted particles to the wells with high precision. In addition, in the particle sorting apparatus according to the related art, if the diameter of the well decreases, it is easy for the liquid droplets to hit a wall surface. For this reason, when sorting object particle are cells, the sorted cells may be damaged and a survival rate of the cells may decrease.

<Entire Configuration of Apparatus>

FIG. 13 is a diagram schematically illustrating a configuration example of a particle sorting apparatus according to this embodiment, FIG. 14A is a diagram schematically illustrating a relation of a side stream and a well plate in the particle sorting apparatus, and FIG. 14B is a diagram schematically illustrating a relation of a side stream and a well plate in the particle sorting apparatus according to the related art. In FIG. 13, the same components as the components of the particle sorting apparatus illustrated in FIG. 1 are denoted with the same reference numerals and detailed explanation thereof is omitted.

As illustrated in FIG. 13, a particle sorting apparatus 31 according to this embodiment includes a microchip 2, a vibration element 3, a charging unit 4, deflection plates 5a and 5b, a waste liquid collection container 35, and a well plate 36. In addition, in the particle sorting apparatus 31 according to this embodiment, the well plate 36 is obliquely arranged in a direction in which an incidence angle theta of a fluid stream S for an opening surface of a well 36a is close to 90 degrees.

<Waste Liquid Collection Container 35>

The waste liquid collection container 35 collects liquid droplets including particles other than sorting object particles or liquid droplets not including particles. As the waste liquid collection container 35, experimental and versatile plastic tubes or glass tubes can be used. A liquid discharge flow channel of the collected liquid droplets may be connected to the waste liquid collection container 35. In addition, the waste liquid collection container 35 is preferably arranged to be exchangeable in the apparatus, at a position where liquid droplet collection by the well plate 36, particularly, movement of the well plate 36 is not disturbed.

<Well Plate 36>

The well plate 36 is used for a PCR method. A plurality of wells (reaction portions) 36a are formed on a substrate and one or more liquid droplets including specific particles are collected to each well 36a. In addition, in the particle sorting apparatus 31 according to this embodiment, the well plate 36 is arranged to be inclined to the fluid stream S. As in the particle sorting apparatus according to the related art illustrated in FIG. 14B, if the well plate 36 is arranged horizontally, the liquid droplets (fluid stream S) are incident from an oblique direction. For this reason, it is easy for the liquid droplets to be deviated from the opening of the well 36a (hit probability reduction) or hit a side wall of the well 36a.

Meanwhile, in the particle sorting apparatus 31 according to this embodiment illustrated in FIG. 14A, because the well plate 36 is inclined to the side stream S, it is easy for the liquid droplets to enter the well 36a and it is difficult for the liquid droplets to hit the side wall of the well 36a. As a result, the particle sorting apparatus 31 according to this embodiment can sort the particles with high precision without damaging the particles. In particular, when sorting object particles are cells, a survival rate after sorting can be increased.

Here, an incidence angle of the well plate 36 is not limited in particular. However, the well plate 36 is preferably arranged obliquely such that the incidence angle theta of the fluid stream S is about 90 degrees with respect to an opening surface of the well 36a. In addition, the number of wells 36a in the well plate 36 used in the particle sorting apparatus 31 according to this embodiment is not limited in particular. However, when the number of wells 36a increases, the above-described effect becomes notable. Also, a shape of the well 36a is not limited and the well may have various shapes. For example, a bottom surface may be planar or curved.

The method of obliquely arranging the well plate 36 is not limited in particular. For example, a method of inclining a plate placing unit of a plate holder holding the well plate 36 at a predetermined angle may be used. FIG. 15 is a lateral view schematically illustrating a state when the well plate is placed on the plate holder in which the plate placing unit is inclined. As illustrated in FIG. 15, a plate placing unit 37a of a plate holder 37 is inclined at an angle alpha according to an angle of a fluid stream S, so that the well plate 36 placed on the plate holder can be inclined to the fluid stream.

Alternatively, the well plate 36 may be inclined to the fluid stream S by placing the well plate 36 or the plate holder on which the well plate 36 is placed on a stage inclined at any angle and inclining the stage.

<Operation>

Next, an operation of the particle sorting apparatus 31 according to this embodiment will be described. The particle sorting apparatus according to this embodiment sequentially moves the well plate 36 by a moving mechanism, such that positions of the fluid stream S and the well 36a of the well plate 36 are matched with each other, and distributes one specific particle or a desired number of specific particles to each well 36a.

At this time, if the well plate 36 is arranged obliquely, a distance of a horizontal direction between the wells 36a changes. For this reason, similar to the case in which the well plate is arranged horizontally, if the well plate 36 is moved, error occurs at the positions of the fluid stream S and the well 36a. Therefore, in the particle sorting apparatus 31 according to this embodiment, a movement control unit to control the moving mechanism is provided and a movement amount of the well plate 36 at the time of sorting is adjusted according to the incidence angle of the well plate 36. Thereby, even when the well plate 36 is arranged obliquely, the positions of the fluid stream S and the well 36a can be matched with each other. As a result, the particles can be sorted with high precision.

When the cells are sorted, a buffer (buffering liquid) is stored previously in the well 36a. In the case of the well plate 36 in which the depth of the well 36a is small, if the well plate is arranged obliquely, the buffer may leak. In addition, in the case in which a bottom of the well 36a is a plane (flat bottom) or the case in which a small amount of buffer is stored in the well 36a, if the well plate 36 is arranged obliquely, a portion covered with the buffer decreases.

Therefore, in the particle sorting apparatus 31 according to this embodiment, the incidence angle of the well plate 36 can be adjusted automatically according to the kind of the well plate 36 and/or the stored buffer amount. FIG. 16 is a flowchart illustrating an operation example of the particle sorting apparatus 31 according to this embodiment. Specifically, as illustrated in FIG. 16, a user inputs the kind (the number or the shape of wells) of the well plate or reads data stored in a barcode or a tag attached to a product and determines the kind of the well plate. In addition, the amount of the buffer stored in the well is input by the user or is determined automatically.

Next, in the inclination control unit provided in the apparatus, the inclination angle of the well plate is determined according to the kind of the well plate and/or the stored buffer amount. In addition, the well plate is inclined by an inclination angle adjusting mechanism such that an angle becomes the determined inclination angle. Then, the well plate movement amount when the well plate is inclined at the predetermined angle is determined by the plate movement control unit provided in the apparatus and the particles are sorted while the movement of the well plate is controlled on the basis of a result thereof.

As such, high-precision sorting can be realized by adjusting the inclination angle of the well plate, according to the kind of the well plate or the amount of the stored buffer. When the well plate having a small number of wells is used, the diameter of the well is large sufficiently for the position precision of the fluid stream S. For this reason, the merit obtained by inclining the well plate decreases. That is, the configuration according to this embodiment is particularly effective to the case of using the well plate in which the number of wells is large and the diameter of the well is small.

Because the well plate is arranged obliquely to the side stream, the particle sorting apparatus according to this embodiment can sort the sorting object particles to the predetermined wells with high precision without damaging the particles.

The particle sorting apparatus according to this embodiment can combine the above-described configuration with the configuration according to the first embodiment, the modification thereof, or the second embodiment. For example, the above-described configuration is combined with the configuration in which the charge application end time in the charging unit is adjusted according to the sizes of the particles included in the liquid droplets, so that the charges can be stably applied to the liquid droplets including the particles having the large size, and sorting precision can be further improved. In addition, the charge application end time is adjusted and the driving voltage of the vibration element is controlled by the excitation control unit on the basis of the state of the fluid stream, so that the break-off point can be maintained at high precision, and liquid droplet formation as well as charging to the liquid droplets can be stabilized.

The present disclosure can take the following configurations.

(1) A particle sorting apparatus including a charging unit configured to apply charges to at least a portion of liquid droplets ejected from an orifice, and a charging control unit configured to adjust a charge application end time for the applied charges according to sizes of particles included in the liquid droplets.

(2) The particle sorting apparatus according to (1), wherein the charging control unit is configured to change a start time of a charge application waveform according to the sizes of the particles included in the liquid droplets.

(3) The particle sorting apparatus according to (1) or (2), wherein the charging control unit is configured to change a charge application duration according to the sizes of the particles included in the liquid droplets.

(4) The particle sorting apparatus according to any of (1) to (3), further including a forward-scattered light detecting unit that includes a light source arranged to illuminate particles flowing along a flow channel and a detector arranged to detect forward-scattered light generated from the particles by the illumination, wherein the charging control unit is configured to adjust the charge application end time on the basis of a detection result from the forward-scattered light detecting unit.

(5) The particle sorting apparatus according to (4), wherein, when an intensity of the forward-scattered light detected by the forward-scattered light detecting unit is equal to or more than a preset threshold value, the charging control unit controls the charging unit such that charge application waveform is delayed as compared with when the intensity of the forward-scattered light is less than the threshold value.

(6) The particle sorting apparatus according to (4) or (5), further including a delay amount calculating unit configured to calculate a delay amount of charge application waveform on the basis of an intensity of the forward-scattered light detected by the forward-scattered light detecting unit, wherein the charging control unit controls the charging unit such that the charge application waveform is delayed according to the delay amount calculated by the delay amount calculating unit.

(7) The particle sorting apparatus according to any of (4) to (6), wherein, when an intensity of the forward-scattered light detected by the forward-scattered light detecting unit is equal to or more than a preset threshold value, the charging control unit controls the charging unit such that a charge application duration is lengthened as compared with when the intensity of the forward-scattered light is less than the threshold value.

(8) The particle sorting apparatus according to any of (4) to (7), further including an application duration calculating unit that calculates a charge application duration on the basis of an intensity of the forward-scattered light detected by the forward-scattered light detecting unit, wherein the charging control unit controls the charging unit such that the charges are applied for the charge application duration calculated by the application duration calculating unit.

(9) The particle sorting apparatus according to any of (1) to (8), wherein the orifice is formed in an exchangeable microchip and the charging unit includes a charging electrode arranged to contact a sheath liquid and/or a sample liquid flowing through a flow channel provided in the microchip.

(10) The particle sorting apparatus according to any of (1) to (9), wherein the orifice is formed in a flow cell.

(11) A particle sorting method including acts of applying charges to at least a portion of liquid droplets ejected from an orifice, and adjusting a charge application end time according to sizes of particles included in the liquid droplets.

(12) A non-transitory computer-readable storage medium storing machine-readable program instructions for causing a charging control unit of a particle sorting apparatus to execute a function of adjusting a charge application end time according to sizes of particles detected in liquid droplets that are ejected from an orifice.

The effects described in the present disclosure are not limitative but exemplary and other effects may be obtained. It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1, 11, 31 Particle sorting apparatus
2 Microchip
3 Vibration element
4 Charging unit
5a, 5b Deflection plate
6a to 6c Collection container
7 Charging control unit
8 Light detecting unit
9 Delay amount calculating unit
10 Application time calculating unit
12 Imaging element (camera)
13, 42 Voltage supplying unit
14 Excitation control unit
15 Position adjusting mechanism
21 Orifice
22 Sample inlet
23 Sheath inlet
24 Suction outlet
35 Waste liquid collection container
36 Well plate
36a Well
37 Plate holder
41 Electrode
71 Delay amount calculating unit
72 Application time calculating unit
S Fluid stream

The invention claimed is:

1. A particle sorting apparatus, comprising:
a charging unit configured to apply charges to at least a portion of a plurality of liquid droplets ejected from an orifice;
a charging control unit configured to adjust a charge application end time for the applied charges based on a plurality of sizes of a plurality of particles included in the plurality of liquid droplets; and
a vibration element configured to vibrate a liquid that flows through a flow channel terminated by the orifice,
wherein the vibration of the liquid is based on a driving voltage from a voltage supplying unit, and
wherein the driving voltage is based on an image that comprises a state of the liquid prior to the ejection of a liquid droplet.

2. The particle sorting apparatus according to claim 1, wherein the charging control unit is further configured to change a start time of a charge application waveform based on the plurality of sizes of the plurality of particles.

3. The particle sorting apparatus according to claim 1, wherein the charging control unit is further configured to change a charge application duration based on the plurality of sizes of the plurality of particles.

4. The particle sorting apparatus according to claim 1, further comprising:
a forward-scattered light detecting unit including a light source illuminate the plurality of particles that flows along the flow channel and a detector to detect forward-scattered light generated from the plurality of particles by the illumination,
wherein the charging control unit is further configured to adjust the charge application end time based on a detection result received from the forward-scattered light detecting unit.

5. The particle sorting apparatus according to claim 4, wherein the charging control unit is further configured to delay a charge application waveform based on an intensity of the forward-scattered light detected by the forward-scattered light detecting unit, and
wherein the intensity of the forward-scattered light is equal to or more than a threshold value.

6. The particle sorting apparatus according to claim 4, further comprising:
a delay amount calculating unit configured to calculate a delay amount of a charge application waveform based on an intensity of the forward-scattered light detected by the forward-scattered light detecting unit,
wherein the charging control unit is further configured to delay the charge application waveform based on the delay amount calculated by the delay amount calculating unit.

7. The particle sorting apparatus according to claim 4,
wherein the charging control unit is further configured to lengthen a charge application duration based on an intensity of the forward-scattered light, and
wherein the intensity of the forward-scattered light is equal to or more than a threshold value.

8. The particle sorting apparatus according to claim 4, further comprising:
an application duration calculating unit configured to calculate a charge application duration based on an intensity of the forward-scattered light detected by the forward-scattered light detecting unit,
wherein the charging unit is further configured to apply the charges for the charge application duration calculated by the application duration calculating unit.

9. The particle sorting apparatus according to claim 1,
wherein the orifice is present in an exchangeable microchip and
wherein the charging unit further includes a charging electrode to contact one of a sheath liquid or a sample liquid that flows through the flow channel present in the microchip.

10. The particle sorting apparatus according to claim 1, wherein the orifice is present in a flow cell.

11. A particle sorting method, comprising:
applying charges to at least a portion of a plurality liquid droplets ejected from an orifice;
adjusting a charge application end time based on a plurality of sizes of a plurality of particles included in the plurality of liquid droplets; and
vibrating a liquid flowing through a flow channel terminated by the orifice,
wherein the vibration of the liquid is based on a driving voltage from a voltage supplying unit, and
wherein the driving voltage is based on an image comprising a state of the liquid prior to the ejecting of a liquid droplet.

12. A non-transitory computer-readable medium having stored thereon computer executable instructions that, when executed by a processor, cause a computer to execute operations, the operations comprising:
applying charges to at least a portion of a plurality liquid droplets ejected from an orifice; and
adjusting a charge application end time based on a plurality of sizes of a plurality of particles detected in the plurality of liquid droplets; and
vibrating a liquid flowing through a flow channel terminated by the orifice,
wherein the vibration of the liquid is based on a driving voltage from a voltage supplying unit, and
wherein the driving voltage is based on an image comprising a state of the liquid prior to the ejecting of a liquid droplet.

\* \* \* \* \*